(12) United States Patent
Thomas et al.

(10) Patent No.: US 6,491,917 B1
(45) Date of Patent: Dec. 10, 2002

(54) ANTIBODY COMPOSITION FOR DEBULKING BLOOD AND BONE MARROW SAMPLES FROM CML PATIENTS

(75) Inventors: Terry E. Thomas, Vancouver (CA); Connie J. Eaves, Vancouver (CA)

(73) Assignee: StemCell Technologies Inc., Vancouver (CA)

( * ) Notice: Subject to any disclaimer, the term of this patent is extended or adjusted under 35 U.S.C. 154(b) by 0 days.

(21) Appl. No.: 09/363,676

(22) Filed: Jul. 30, 1999

Related U.S. Application Data

(60) Provisional application No. 60/094,926, filed on Jul. 31, 1998.

(51) Int. Cl.⁷ .................. A61K 39/395; C07K 16/00
(52) U.S. Cl. ................. 424/140.1; 530/387.7; 530/388.1; 530/388.8; 530/391.1
(58) Field of Search .............. 424/140.1; 530/387.7, 530/388.1, 388.8, 391.9

(56) References Cited

U.S. PATENT DOCUMENTS 5,260,416 A * 11/1993 Chang .................... 530/327
5,877,299 A * 3/1999 Thomas et al. ............ 530/413

OTHER PUBLICATIONS

Guyotat et al, "Pre–clinical evaluation of anti–lacto–N–fucopentaose III (CD15) monoclonal antibodies for ex–vivo bone marrow purging in acute myeloid leukemia." Bone Marrow Transplantation, vol. 6, No. 6, pp. 385–390, (abstract), Dec. 1990.*

Hawkins, T.E. et al., 1997, Bone Marrow Transplantation, 20:409–413.

Martín–Henao, G.A. et al., 1996., Bone Marrow Transplantation, 18: 603–609.

* cited by examiner

*Primary Examiner*—Anthony C. Caputa
*Assistant Examiner*—Karen A. Canella
(74) *Attorney, Agent, or Firm*—Bereskin & Parr; Micheline Gravelle

(57) ABSTRACT

The present invention relates to an antibody composition which contains antibodies specific for glycophorin A, CD2, CD3, CD14, CD15, CD16, CD19, CD24, CD56, CD66b and IgE antigens. A negative selection process is also provided for use on blood and bone marrow samples from a patient with chronic myeloid leukemia to recover cell preparations depleted of lineage committed cells. The invention also relates to kits for carrying out this process and to the cell preparations prepared by the process.

13 Claims, 3 Drawing Sheets

US 6,491,917 B1

ANTIBODY COMPOSITION FOR DEBULKING BLOOD AND BONE MARROW SAMPLES FROM CML PATIENTS

This application claims benefit from U.S. provisional application Ser. No. 60/094,926 filed on Jul. 31, 1998 which is incorporated herein by reference in its entirety.

FIELD OF THE INVENTION

The present invention relates to a method of depleting normal and transformed lineage committed cells from a sample from a patient with chronic myeloid leukemia.

BACKGROUND OF THE INVENTION

Chronic myeloid leukemia (CML) is a monoclonal expansion of a transformed pluripotent stem cell (Fialkow et al., 63:125, 1977, American Journal of Medicine). Myeloid cells, erythroid cells and less frequently lymphocytes arise from the leukemic clone (Bakhshi et al., New Eng. J. Med. 309:826, 1983). CML is characterized in more than 90% of patients by the rearrangement between the break cluster region (BCR gene, located on chromosome 22) and the ABL gene (located on chromosome 9) (Bartran et al., Nature 306:277, 1983).

Although patients with CML may have a prolonged course, the disease is invariably lethal. Bone marrow transplantation is the treatment of choice for this patient population with a curative rate of 90% in some centres. However, for 60% of patients this therapy may not be available either due to the lack of a suitable donor due to differences in human leukocyte antigens (HLA) or the age of the recipient.

For these reasons, other treatment options have been evaluated for their ability to remove the leukemic cells from the harvested material without depleting or damaging the co-existing benign (non-malignant) stem cells. The methods have included various drug regiments (Degliantoni et al., Blood 65:753, 1985) or the culture of the patient cells using the Dexter (long term culture) system which was shown to preferentially support the proliferation of benign stem cells as compared to malignant cells (Barnett et al., Bone Marrow Transplant 4:345, 1985).

Clinical experience has confirmed that although the leukemic burden has been greatly reduced using such protocols, the malignant cells in most patients have not been entirely eradicated and patients relapse with their original disease. (Coutintro et al., Progress in Clinical and Biological Research 333:415, 1990 and Deisseroth et al., Blood 83:3068, 1994) In addition, the high incidence of graft failure also suggests that certain types of treatment may have had adverse effects on the non-malignant stem cells (Talpaz et al., Blood 85:3257, 1995 and Daley and Goldman, Exp. Hematol. 21:731, 1993).

Further analysis of this disease has focussed on dissecting out certain populations of primitive cells in an attempt to understand at what stage the clonal abnormality occurs (Verfaille et al., Blood 87:4770, 1996). These studies may be limited by the low frequency of primitive cells due to the clonal proliferation of lineage committed cells. Further studies of this disease may be facilitated if the mature lineage committed "contaminating" cells could be reduced or eliminated.

SUMMARY OF THE INVENTION

The present inventors have developed an antibody composition for use in preparing cell preparations depleted of normal and transformed lineage committed cells, for example from blood or bone marrow samples from patients with chronic myeloid leukemia. The antibodies in the antibody composition are specific for selected markers associated with lineage committed cells. In particular, the present inventors have found that using an antibody composition containing antibodies specific for glycophorin A, CD2, CD3, CD14, CD15, CD16, CD19, CD24, CD56, CD66b and IgE gives a cell preparation enriched for hematopoietic stem cells and progenitor cells and depleted of committed lineage or differentiated cells.

Accordingly, the present invention relates to an antibody composition comprising antibodies specific for glycophorin A, CD2, CD3, CD14, CD15, CD16, CD19, CD24, CD56, CD66b and IgE which gives a cell preparation depleted of lineage committed cells.

The present invention also provides an antibody composition comprising antibodies specific for glycophorin A, CD2, CD3, CD14, CD16, CD19, CD24, CD56, CD66b and IgE. Such a composition can be used in combination with antibodies to CD15 to prepare a cell preparation depleted of lineage committed cells.

The present invention also includes a negative selection method for depleting lineage committed cells from a sample from a patient with chronic myeloid leukemia comprising:

(a) reacting the sample with an antibody composition comprising antibodies specific for glycophorin A, CD2, CD3, CD14, CD15, CD16, CD19, CD24, CD56, CD66b and IgE under conditions so that conjugates between the antibodies and cells in the sample having the antigens glycophorin A, CD2, CD3, CD14, CD15, CD16, CD19, CD24, CD56, CD66b and IgE on their surfaces;

(b) removing the conjugates; and (c) recovering a cell preparation which is depleted of lineage committed cells.

The antibody composition of the invention may be used to prepare cell preparations from patients with chronic myeloid leukemia that are depleted of matured differentiated or lineage committed cells and can withstand freezing.

In a preferred embodiment, the sample is first treated with an antibody to CD15 and then it is treated with a cocktail or composition comprising the remaining antibodies to glycophorin A, CD2, CD3, CD14, CD16, CD19, CD24, CD56, CD66b and IgE.

The present invention also relates to a kit useful for performing the processes of the invention comprising antibodies specific for glycophorin A, CD2, CD3, CD14, CD15, CD16, CD19, CD24, CD56, CD66b and IgE and instructions for performing the process of the invention.

Other features and advantages of the present invention will become apparent from the following detailed description.. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Antibody Composition

Figure 1:
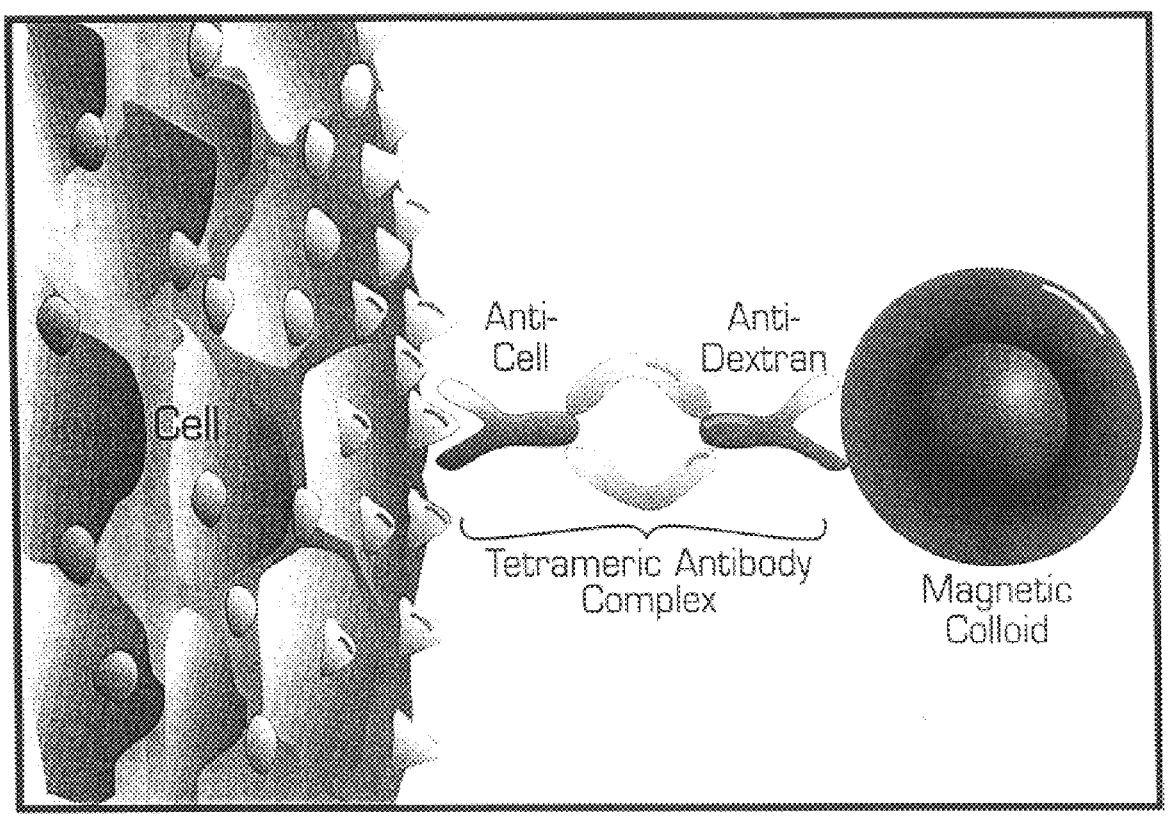
FIG. 1 is a schematic drawing showing Magnetic Labelling of Human Cells: Cells are cross-linked to magnetic particles using tetrameric antibody complexes comprised of two murine IgG$_1$ monoclonal antibodies held in tetrameric array by two rat anti-mouse IgG$_1$ monoclonal antibody molecules. One murine antibody molecule recognizes the cell surface antigen and the other recognizes the dextran on the magnetic particle.

In one embodiment, the present invention relates to an antibody composition comprising antibodies specific for the antigens glycophorin A, CD2, CD3, CD14, CD15, CD16, CD19, CD24, CD56, CD66b and IgE which are present on the surface of differentiated or lineage committed cells.

In another embodiment, the present invention relates to an antibody composition comprising antibodies specific for the antigens glycophorin A, CD2, CD3, CD14, CD16, CD19, CD24, CD56, CD66b and IgE which are present on the surface of differentiated or lineage committed cells.

Within the context of the present invention, antibodies are understood to include monoclonal antibodies and polyclonal antibodies, antibody fragments (e.g., Fab, and F(ab')$_2$) and recombinantly produced binding partners.

Polyclonal antibodies against selected antigens on the surface of human cells may be readily generated by one of ordinary skill in the art from a variety of warm-blooded animals such as horses, cows, various fowl, rabbits, mice, or rats.

Preferably, monoclonal antibodies are used in the antibody compositions of the invention. Monoclonal antibodies specific for selected antigens on the surface of human cells may be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in Escherichia coli for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques).

Similarly, binding partners may be constructed utilizing recombinant DNA techniques. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. The primers may be utilized to amplify heavy or light chain variable regions, which may then be inserted into vectors such as ImmunoZAP™ H or ImmunoZAP™ L (Stratacyte), respectively. These vectors may then be introduced into E. coli for expression. Utilizing these techniques, large amounts of a single-chain protein containing a fusion of the $V_H$ and $V_L$ domains may be produced (See Bird et al., Science 242:423–426, 1988). In addition, such techniques may be utilized to change a "murine" antibody to a "human" antibody, without altering the binding specificity of the antibody.

Antibodies against selected antigens on the surface of differentiated or lineage committed cells may also be obtained from commercial sources.

Antibodies may be selected for use in the antibody compositions of the invention based on their ability to deplete targeted differentiated cells and recover non-targeted cells (i.e. progenitor and stem cells, or specific differentiated cells) in magnetic cell separations as more particularly described herein, and in co-pending U.S. patent application Ser. Nos. 08/566,295 and 09/088,227, and U.S. Pat. Nos. 5,514,340 and 5,877,299 which are incorporated in their entirety herein by reference. In general, an antibody is selected that gives approximately a 3 log depletion of the target cell, with greater than 75% recovery of CD34$^+$ cells (bone marrow, mobilized blood and cord blood) or non-targeted lymphocytes (steady state blood), in test magnetic cell separations as described herein.

The anti-glycophorin A antibodies contained in the antibody composition of the invention are used to label erythrocytes. Examples of monoclonal antibodies specific for glycophorin A are 2B7.1 (StemCell Technologies) 10F7MN (U.S. Pat. No. 4,752,582, Cell lines: ATCC accession numbers HB-8473, HB-8474, and HB-8476), and D2.10 (Immunotech, Marseille, France). The concentration of anti-glycophorin A antibodies used in the antibody composition are generally less than the concentration that will cause agglutination (i.e. 3–10 $\mu$g/ml). Preferably the concentration of anti-glycophorin A antibodies used in the antibody composition is between about 0.5 to 5 $\mu$g/ml, preferably 1 to 2 $\mu$g/ml.

The antibodies against CD15 are used to label mature myeloid cells. Examples of monoclonal antibodies specific for CD15 include DU HL60-3 (Sigma, Saint Louis, Miss.) MMA (Becton Dickinson, Mountain View, Calif.), H198 (Pharmingen, San Diego, Calif.) and 80H5 (Immunotech, Marseille, France). The concentration of CD15 antibodies used in the antibody composition is usually 3 $\mu$g/ml. Preferably the concentration of CD15 antibodies used in the antibody composition is between about 1 to 3 $\mu$g/ml preferably 3 $\mu$g/ml.

The antibodies against CD2, CD3, CD19, CD24 and CD56 in the antibody composition of the invention are used to label B and T-lymphocytes and NK cells. Examples of monoclonal antibodies specific for CD2, CD3, CD19, CD24 and CD56 are 6F10.3 (Immunotech, Marseille, France) SK7 (Becton Dickinson) L1CHT1 (Immunotech, Marseille, France) and 4G7 (Beckon Dickinson, Mountain View, Calif.), 32D12 (Dr. Steinar Funderud, Institute for Cancer Research, Department of Immunology, Oslo, Norway) and ALB9 (Immunotech, Marseille, France) and T199 (Immunotech, Marseille, France) or M431 (Beckon Dickinson, Mountain View, Calif.). The concentration of each of the monoclonal antibodies against CD2, CD3, CD19, CD24 and CD56 for an antibody composition of the invention is about 1 to 3 μg/ml, preferably 3 μg/ml for each antibody concentration, the preferred concentration is 3.0 μg/ml.

The antibodies against CD14, CD16 and CD66b in the antibody compositions of the invention are used to label monocytes and granulocytes. Examples of monoclonal antibodies specific for CD14, CD16 and CD66b are MEM15 and MEM18 (Dr. Vaclav Horejsi, Institute of Molecular Genetics Academy of Sciences of the Czech Republic, Praha, Czech Republic; Cedarlane Laboratories, Hornby, Ontario, Canada); MEM 154 (Dr. Vaclav Horejsi, Institute of Molecular Genetics Academy of Sciences of the Czech Republic, Praha, Czech Republic; Cedarlane Laboratories, Hornby, Ontario, Canada); and, B13.9 (CLB, Central Laboratory of the Netherlands, Red Cross, Blood Transfusion Service) and 80H3 (Immunotech, Marseille, France), respectively. The concentration of each of the monoclonal antibodies against CD14, CD16 and CD66b for an antibody composition of the invention is about 1 to 3 μg/ml, preferably 3 μg/ml, except 2 μg for CD16 (MEM 154)

The antibodies to IgE molecules bind IgE antibodies and mast cells and basophils. Examples of monoclonal antibodies specific for IgE include 47-18 (Pharmingen, San Diego, Calif.) and E124.2.8 (Immunotech, Marseille, France). Preferably the concentration of anti-IgE antibodies used in the antibody composition is between about 1 to 3 μg/ml, preferably 3 μg/ml.

II. Processes for Preparing Cell Preparations

The antibody composition of the invention may be used to prepare cell preparations from patients with chronic myeloid leukemia (CML) that are depleted of matured differentiated or lineage committee cells and can withstand freezing. Preferably, the antibody composition can be used on blood or bone marrow samples from patients with CML. The negative selection method of the invention is advantageous because the desired stem cells and progenitor cells that are recovered in the method are not labelled or coated with antibodies. In addition, additional processing steps such as positive selection protocols are not required in order to recover a cell preparation enriched in stem cells and progenitor cells but depleted of lineage committed or differentiated cells.

Accordingly, the present invention provides a negative selection method for depleting differentiated or lineage committed cells from a sample from a patient with chronic myeloid leukemia comprising:

(a) reacting the sample with an antibody composition comprising antibodies specific for glycophorin A, CD2, CD3, CD14, CD15, CD16, CD19, CD24, CD56, CD66b and IgE under conditions so that conjugates form between the antibodies and cells in the sample having the antigens glycophorin A, CD2, CD3, CD14, CD15, CD16, CD19, CD24, CD56, CD66b and IgE on their surfaces;

(b) removing the conjugates; and (c) recovering a cell preparation which is depleted of lineage committed cells.

Preferably, the present invention provides a method for depleting differentiated or lineage committed cells from a sample from a patient with chronic myeloid leukemia comprising:

(a) reacting the sample with an antibody specific for CD15 under conditions so that conjugates form between the antibodies and cells in the sample having the antigen CD15 on their surfaces;

(b) reacting the sample from step (a) with an antibody composition comprising antibodies specific for glycophorin A, CD2, CD3, CD14, CD16, CD19, CD24, CD56, CD66b and IgE under conditions so that conjugates form between the antibodies and the cells in the sample having the antigens glycophorin A, CD2, CD3, CD14, CD16, CD19, CD24, CD56, CD66b and IgE on their surfaces;

(c) removing the conjugates; and (d) recovering a cell preparation which is depleted of lineage committed cells.

Prior to conducting the above described methods of the invention the sample may be treated to obtain low density cells from the sample, for example by density centrifugation.

Conditions which permit the formation of cell conjugates may be selected having regard to factors such as the nature and amounts of the antibodies in the antibody composition, and the estimated concentration of targeted human cells in the sample.

The antibodies in the antibody composition may be labelled with a marker or they may be conjugated to a matrix. Examples of markers are biotin, which can be removed by avidin bound to a support, and fluorochromes, e.g. fluorescein, which provide for separation using fluorescence activated sorters. Examples of matrices are magnetic beads, which allow for direct magnetic separation (Kemshead 1992), panning surfaces e.g. plates, (Lebkowski, J. S, et al., (1994), J. of Cellular Biochemistry supple. 18b:58), dense particles for density centrifugation (Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.), adsorption columns (Berenson et al. 1986, Journal of Immunological Methods 91:11–19.), and adsorption membranes (Nordon et al. 1994, Cytometry 16:25–33). The antibodies may also be joined to a cytotoxic agent such as complement or a cytotoxin, to lyse or kill the targeted differentiated cells.

The antibodies in the antibody composition may be directly or indirectly coupled to a matrix. For example, the antibodies in the composition of the invention may be chemically bound to the surface of magnetic particles for example, using cyanogen bromide. When the magnetic particles are reacted with a sample, conjugates will form between the magnetic particles with bound antibodies specific for antigens on the surfaces of the differentiated cells, and the differentiated cells having the antigens on their surfaces.

Alternatively, the antibodies may be indirectly conjugated to a matrix using antibodies. For example, a matrix may be coated with a second antibody having specificity for the antibodies in the antibody composition. By way of example, if the antibodies in the antibody composition are mouse IgG antibodies, the second antibody may be rabbit anti-mouse IgG.

The antibodies in the antibody composition may also be incorporated in antibody reagents which indirectly conjugate to a matrix. Examples of antibody reagents are bispecific antibodies, tetrameric antibody complexes, and biotinylated antibodies.

Bispecific antibodies contain a variable region of an antibody in the antibody composition of the invention, and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

A tetrameric immunological complex may be prepared by mixing a first monoclonal antibody which is capable of binding to at least one antigen on the surface of a matrix, and a second monoclonal antibody from the antibody composition of the invention. The first and second monoclonal antibodies are from a first animal species. The first and second antibodies are reacted with an about equimolar amount of monoclonal antibodies of a second animal species which are directed against the Fc-fragments of the antibodies of the first animal species. The first and second antibodies may also be reacted with an about equimolar amount of the $F(ab')_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

The antibodies of the invention may be biotinylated and indirectly conjugated to a matrix which is labelled with (strept) avidin. For example, biotinylated antibodies contained in the antibody composition of the invention may be used in combination with magnetic iron-dextran particles that are covalently labelled with (strept) avidin (Miltenyi, S. et al., Cytometry 11:231, 1990). Many alternative indirect ways to specifically cross-link the antibodies in the antibody composition and matrices would also be apparent to those skilled in the art.

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. (1992) in J. Hematotherapy, 1:35–44, at pages 36 to 39, and Ziolo et al. Science (1994) 257:219 which are incorporated herein by reference. Colloidal particles of dextran-iron complex are preferably used in the process of the invention. (See Molday, R. S. and McKenzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother. 2:297 (1993); and U.S. Pat. No. 4,452,733, which are each incorporated herein by reference).

FIG. 1 is a schematic representation of magnetic cell labeling using tetrameric antibody complexes and colloidal dextran iron. Cells are cross-linked to magnetic particles using tetrameric antibody complexes comprised of two murine $IgG_1$ monoclonal antibodies held in tetrameric array by two rat anti-mouse $IgG_1$ monoclonal antibody molecules. One murine antibody molecule recognizes the cell surface antigen and the other recognizes the dextran on the magnetic particle.

In accordance with the magnetic separation method, the sample containing the progenitor and stem cells to be recovered, is reacted with the above described antibody reagents, preferably tetrameric antibody complexes, so that the antibody reagents bind to the targeted differentiated cells present in the sample to form cell conjugates of the targeted differentiated cells and the antibody reagents. The reaction conditions are selected to provide the desired level of binding of the targeted differentiated cells and the antibody reagents. Preferably the sample is incubated with the antibody reagents for a period of 5 to 60 minutes at either 4° C. or ambient room temperature. The concentration of the antibody reagents is selected to optimize cell labeling in a sample of $2–8 \times 10^7$ nucleated cells per ml. Generally, the concentration is between about 0.1 to 50 µg/ml of sample. The magnetic particles are then added and the mixture is incubated for a period of about 5 minutes to 30 minutes at the selected temperature. The sample is then ready to be separated over a magnetic filter device. Preferably, the magnetic separation procedure is carried out using the magnetic filter and methods described in co-pending U.S. Pat. No. 5,514,340 to Lansdorp and Thomas which is incorporated in its entirety herein by reference.

The sample containing the magnetically labelled cell conjugates is passed through the magnetic filter in the presence of a magnetic field. In a preferred embodiment of the invention, the magnet is a permanent gap magnet with 0.5–2.0" diameter bore and having a magnetic field of 0.5–2 Tesla. The magnetically labelled cell conjugates are retained in the high gradient magnetic column and the materials which are not magnetically labelled flow through the column after washing with a buffer.

The preparation containing non-magnetically labelled cells may be analyzed using procedures such as flow cytometry. The ability of the cells in the preparation to produce colony-forming cells or long term culture initiating cells (LTCIC) in culture may also be assessed. The efficiency of the separation procedure may also be determined by monitoring the recovery of $CD34^+$ cells, $CD34^+$ $CD38^-$ cells and colony forming cells.

III. Uses

Methods and compositions of the invention may be used in processing samples from patients with chronic myeloid leukemia including samples of blood or bone marrow. It has been known for over 2 decades that the maturing leukemic myeloid cells in CML are lighter than their normal counterparts (Moore, MAS, et al., (1973), J. Natl. Cancer Inst. 50:603). Hence they are more prevalent in the low density fraction of cells obtained using standard commercial media that efficiently separate normal red cells and granulocytes. In addition, blood and marrow samples from many CML patients contain elevated numbers of basophils and their precursors as part of their increased granulopoiesis. Such myeloid cells do not survive freezing/thawing and debris from their lysis hampers the recovery of other cells in the sample. When a blood or bone marrow sample from a patient with chronic myeloid leukemia is frozen and then thawed generally only 2% of CD34 cells are recovered. Approximately 10% of colony forming cells (CFC) are recovered. However, when the sample is first processed using the antibody composition of the invention, the inventors have shown that there is 60% recovery of $CD34^+$ cells and CFC. This is advantageous as it permits the storage of samples from chronic myeloid leukemia patients allowing for further study of the disease and the cells involved in the disease.

IV. Kit

The present invention also relates to a kit containing the antibody composition of the composition of the invention for use in making cell preparations from patients with chronic myeloid leukemia which are depleted of differentiated or lineage committed cells. The kit includes instructions for performing the process of depleting cells from samples from such patients as well as antibodies specific for glycophorin A, CD2, CD3, CD14, CD15, CD16, CD19, CD24, CD56, CD66b and IgE and reagents helpful in carrying out the process of the invention. Also optionally included are containers and other materials appropriate for conducting the process of the invention.

The following examples provide illustrations of the present invention and in no way serve to narrow the scope of the claims.

EXAMPLES

Example 1

Figure 2:
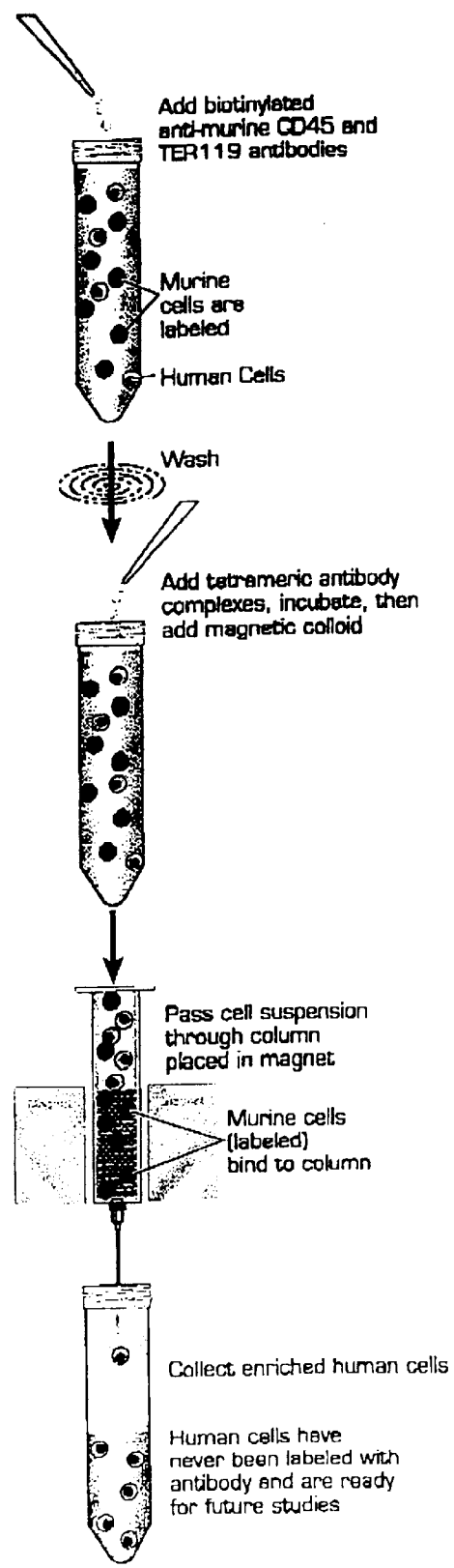
FIG. 2 is a schematic drawing showing the cell separation procedure for CML samples.

Lineage committed cells were depleted from samples of blood (Tables 1A and 1B) and bone marrow (Tables 2A and 2B) from CML patients by treating the sample first with antibodies to CD15 and then with tetrameric antibody complexes recognizing CD2, CD3, CD14, CD16, CD19, CD24, CD56, CD66b, IgE, glycophorin A and biotin. The combination of antibodies to CD15 and the tetrameric antibody complexes is referred to herein as "the CML debulking cocktail". Low density cells were obtained using Ficoll density centrifugation. The cells were then washed twice with phosphate buffered saline (PBS), resuspended at $5 \times 10^7$ cell/mL in PBS plus 2% fetal calf serum (FCS) and incubated for 30 minutes on ice with 3 µg/mL biotinylated anti-CD15. After a single wash with PBS +2% FCS the cells were resuspended again at $5 \times 10^7$ /mL and incubated for 30 minutes on ice with the remainder of the CML debulking cocktail (tetrameric complexes recognizing CD2, CD3, CD14, CD16, CD19, CD24, CD56, CD66b, IgE, glycophorin A and biotin). Colloidal magnetic dextran iron particles were added to the cells, the cells incubated for an additional 30 minutes and then passed through a magnetic column. FIG. 2 is a schematic drawing showing the cell separation procedure for CML samples. The cells collected in the column flow through were depleted of mature lineage committed cells.

Removal of mature cells enriches for immature $CD34^+$ cells and progenitors which have the potential to form hematopoietic colonies in semi-solid medium (Colony Forming Cells—CFC). The purity of $CD34^+$ cells obtained following processing CML samples with the CML debulking cocktail ranged from 54–79% for blood samples and 36–80% for bone marrow samples. The fold enrichment of $CD34^+$ cells depends on the frequency of $CD34^+$ cells in the start cell suspension which varies greatly (0.3%–11% for these samples). The recovery of $CD34^+$ cells and CFC also varies greatly. This was due to abnormal co-expression of mature lineage markers and $CD34^+$ on CML cells and the ability of some CML cells which express lineage markers to form colonies in culture (see later discussion). More primitive hematopoietic progenitors can be assayed by the potential for colony formation in semi-solid medium after 6 weeks of culture in liquid long-term culture medium. The frequency and recovery of these primitive cells (week 6 CFC) following processing with the CML debulking cocktail (method outlined above) was determined for one CML blood and one CML bone marrow sample (Table 2C). These primitive hematopoietic progenitors were highly enriched with essentially 100% recovery.

Example 2

Lineage committed cells were depleted from samples of blood and bone marrow from CML patients using a standard lineage depletion cocktail of antibodies (CD2, CD3, CD14, CD16, CD19, CD24, CD56, CD66b and glycophorin-A) designed to enrich for hematopoietic progenitors from normal peripheral blood and bone marrow and the CML debulking cocktail (which further includes antibodies to CD15 and IgE) as described in Example 1. Direct comparisons of these 2 cocktails in processing CML samples show the CML debulking cocktail provides slightly higher purities and enrichments of $CD34^+$ cells ($p<0.05$) and did not compromise the recovery of $CD34^+$ cells (Table 3A). Both cocktails offered similar enrichment of Colony Forming Cells (CFC) (Table 3B).

Example 3

The recovery of $CD34^+$ cells and CFC from CML samples following freezing and thawing was tested with and without processing with the CML debulking cocktail. Samples of low density cells from CML patients were divided in two. Half the cells were directly frozen and the other half were processed with the CML debulking cocktail (method outlined in Example 1) and then frozen. The recovery of $CD34^+$ cells and CFC were assessed. Percent recoveries were calculated relative to the same original starting value in the fresh low density cell population. Thus in the case of the cells processed with the CML debulking cocktail the calculated recoveries include losses due to lineage depletion as well as freezing and thawing. The recoveries of both $CD34^+$ cells and CFC were improved several-fold ($p<0.85$) (mean 36 fold increase in recovery of $CD34^+$ cells and mean 7 fold increase in recovery of CFC) by prior processing with the CML debulking cocktail according to Example 1 (Table 4).

Summary of Results

Figure 3:
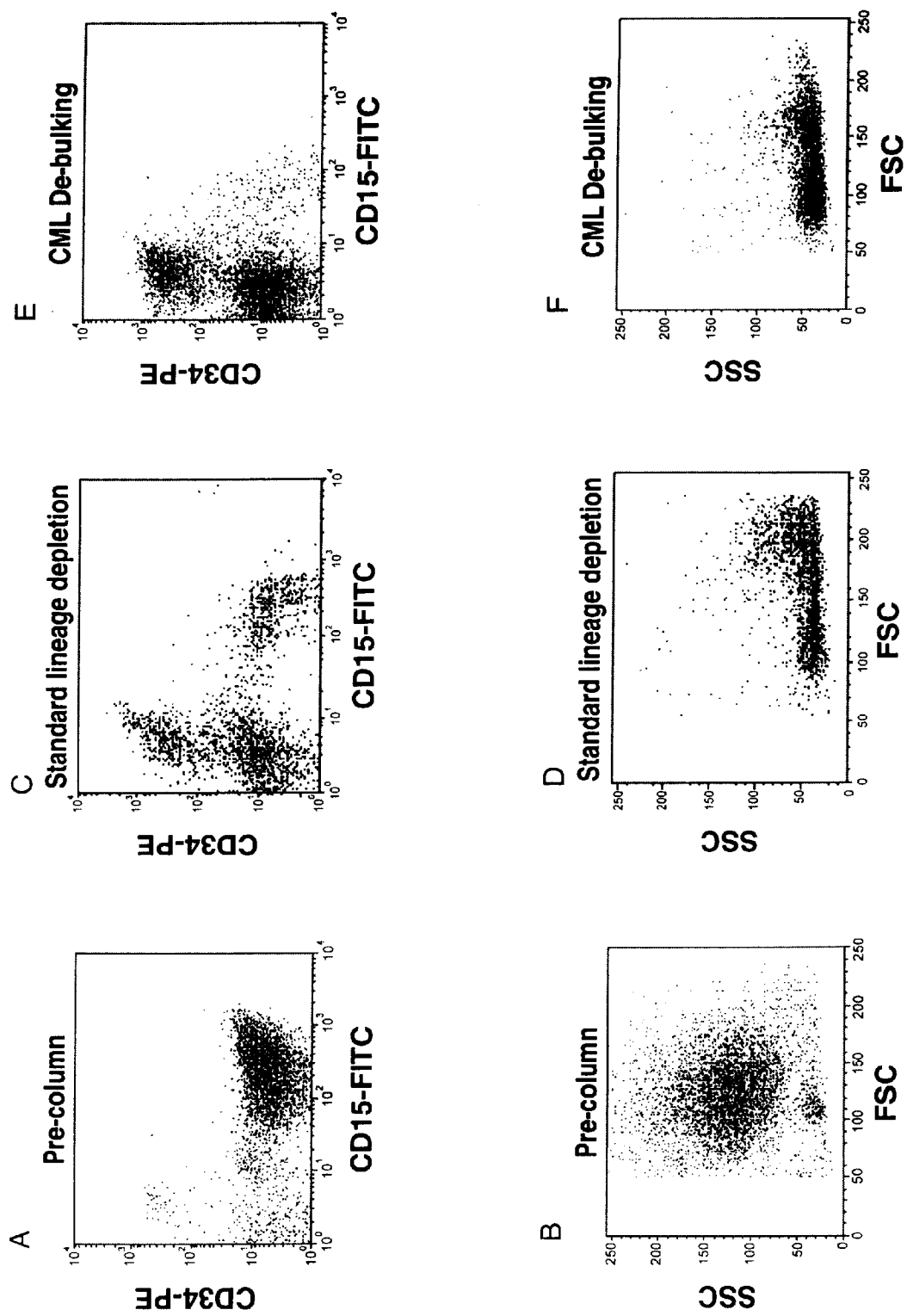
FIG. 3 shows FACS dotplots of CML bone marrow before and after processing with the standard lineage depletion cocktail and the CML debulking cocktail. Both the side and forward scatter of the cells are shown (FIGS. 3B, 3D and 3F), and the cells were stained with anti CD34-PE and anti CD15-FITC (FIGS. 3A, 3C and 3E).

Representative FACS dotplots from a CML patient sample in which the percentage of $CD34^+$ cells in the input fraction was only 1.7% are shown in FIG. 3A. The $CD34^+$ population is discreet whereas the $CD15^+$ population is large and represents granulocytes, basophils and less mature myeloid cells which are present in CML (See FIG. 3B high SSC). After separation using the standard lineage depletion cocktail (FIG. 3C) there is enrichment of the $CD34^+$ population, the resulting purity having increased to 28% (a 16 fold increase from the start sample). However, a large distinct population of $CD34^-$ cells remained which following staining was confirmed to be partially $CD15^+$ cells (FIG. 3C). When the CML Debulking cocktail described in Example 1 (which contains two extra antibodies against CD15 and IgE) was used on the same start material, the numbers of residual cells expressing CD15 diminished leading to a greater overall purity and enrichment of $CD34^+$ cells (FIG. 3E) and to a less heterogenous side scatter profile (FIG. 3F). The frequency of $CD15^+$ cells in the start fraction was 87%. This decreased to 21% following separation with the standard lineage depletion cocktail, but where the CML Debulking cocktail of Example 1 was used, this was reduced further to 2.8%.

The comparative recoveries of $CD34^+$ cells and CFC was assessed following freezing and thawing of CML patient samples which had either not been processed or which had been processed with the CML Debulking cocktail of Example 1. The results are shown in Table 4. The percent recovery data shown in this figure includes cell losses occurring in a cell separation procedure and during the freeze/thaw cycle. Processing with the CML debulking cocktail increases the recovery of $CD34^+$ cells from 1.7 to 61% and recovery of CFC from 8.3 to 58%. Use of the CML debulking cocktail has made cryopreservation of CML samples a viable option for researchers studying the biology of CML.

All publications, patents and patent applications are herein incorporated by reference in their entirety to the same extent as if each individual publication, patent or patent application was specifically and individually indicated to be incorporated by reference in its entirety.

While what is shown and described herein constitutes various preferred embodiments of the subject invention, it will be understood that various changes can be made to such embodiments without departing from the subject invention, the scope of which is defined in the appended claims.

DETAILED REFERENCES

Bakhshi A, Minowada J, Arnold A, Cossman J, Jensen J P, Whang-Peng J, Waldmann, T A and Korsmeyer, S J: Lymphoid blast crises of chronic myelogenous leukemia represent stages in the development of B-cell precursors. New England Journal of Medicine 309:826, 1983

Barnett M J, Eaves C J, Phillips G L, Kalousek D K, Klingemann H G, Lansdorp T M, Reece C E, Shepherd J D, Shaw G J, and Eaves A C: Successful autografting in chronic myeloid leukemia after maintenance of marrow in culture. Bone Marrow Transplant. 4:345, 1989.

Bartram C R, de Klein A, Hagemeijer A, van Agthoven T, van Kessel A G, Bootsma D, Grosveld G, Ferguson-Smith M A, Davies T, Stone M, Heisterkamp N, Stephenson J R and Groffen J: Translocation of c-abl oncogene correlates with the presence of a Philadelphia chromosome in chronic myelocytic leukemia. Nature 306:277, 1983.

Coutinho L H, Dexter T M, Harrison C, Morgenstern G, Chang J, Testa N G: The use of cultured bone marrow cells in autologous transplantation. Progress in Clinical and Biological Research 333:415, 1990.

Daley G Q, Goldman J M: Autologous transplant for CML revisited. Exp. Hematol. 21:734, 1993.

Degliantoni G, Rizzoli V, Mangoni L: In vitro restoration of polyclonal hematopoiesis in a chronic myelogenous leukemia after in vitro treatment with 4-hydroperoxycyclophosphamide. Blood 65:753, 1985.

Deisseroth A B, Zu Z, Claxton D, Hanania E G, Fu S, Ellerson D, Goldberg L, Thomas M, Janieck K, Anderson W F, Hester J, Korbling M, Durett A, Moen R, Berenson R, Heinfeld S, Hamer J, Calvert L, Tibbits P, Talpaz M, Kantarjian H, Champlin R and Reading C: Genetic marking shows that Ph+ cells present in autologous transplants of chronic myelogenous leukemia (CML) contribute to relapse after autologous bone marrow in CML. Blood 83:3068, 1994.

Fialkow P J, Jacobson R J, Papayannopoulou T: Chronic myelocytic leukemia: clonal origin in a stem cell common to the granulocyte, erythrocyte, platelet and monocyte/macrophage. American Journal of Medicine 63:125, 1977.

Kemshead, J. T., J. Hematotherapy, 1:35–44, 1992.

Moore M A S, Williams N and Metcalf D: In vitro colony formation by normal and leukemic human hematopoietic cells: Characterization of the colony forming cell. J. Natl. Cancer Inst., Vol. 50, p. 603, 1973.

Nordon R E, Milthorpe B K, Schindhelm K, and Slowiaczek P R: An Experimental Model of Affinity Cell Separation. Cytometry 16:25–33, 1994.

Talpaz M, Kantarjian H, Liang J, Calvert L, Haner J, Tibbits P, Durett A, Claxton D, Ciralt S, Khari I, Przepiorka D, van Besien K, Andersson B, Mehra R, Gajewski J, Scong D, Hester J, Estay E, Korbling M, Pollicardo N, Berenson R, Hamfeld S, Charuplin R and Deisseroth A B: Percentage of Philadelphia chromosome (Ph)-negative and ph-positive cells found after autologous transplantation for chronic myelogous leukemia depends on percentage of diploid cells induced by conventional-dose chemotherapy before collection of autologous cells. Blood 85:3257, 1995.

Verfaillie C M, Bhatia R, Miller W, Mortari F, Roy V, Burger S, McCullough J, Stieglbauer K, Dewald G, Heimfeld S, Miller J S, McGlave P B: BCR/ABL-negative primitive progenitors suitable for transplantation can be selected from the marrow of most early-chronic phase but not accelerated-phase chronic myelogenous leukemia patients. Blood 87:4770, 1996.

TABLE 1A

The Purity and Recovery of CD34+ cells in the CML blood samples before and after processing with CML Debulking cocktail.

| Sample number | % CD34+ cells in CML blood | % CD34+ cells following CML Debulking | Fold Enrichment | % Recovery of CD34+ cells |
|---|---|---|---|---|
| 1 | 11 | 56 | 5 | 12 |
| 2 | 4.7 | 54 | 12 | 3.4 |
| 3 | 1.8 | 79 | 45 | 23 |
| Mean | 5.8 | 63 | 21 | 13 |

TABLE 1B

The Frequence and Recovery of CFC in the CML blood sample before and after processing with CML Debulking cocktail.

| Sample number | Frequence of CFC in CML blood | Frequency of CFC following CML Debulking | Fold Enrichment | % Recovery of CFC |
|---|---|---|---|---|
| 1 | 1:19 | 1:6.8 | 2.9 | 6.7 |
| 2 | 1:133 | 1:4.4 | 30 | 8.9 |
| 3 | 1:127 | 1:1.6 | 79 | 41 |
| Mean | 1:93 | 1:4.2 | 38 | 19 |

TABLE 2A

The Purity and Recovery of CD34+ cells in CML bone marrow samples before and after processing with the CML Debulking cocktail.

| Sample number | % CD34+cells in CML bone marrow | % CD34+cells following CML Debulking | Fold Enrichment | Recovery of CD34+ cells |
|---|---|---|---|---|
| 1 | 4.6 | 80 | 17 | 40.7 |
| 2 | 1.7 | 36 | 21 | 63.5 |
| 3 | 0.3 | 55 | 161 | 100 |
| Mean | 2.2 | 57 | 66 | 68.1 |

TABLE 2B

The Frequency and Recovery of CFC in CML bone marrow samples before and after processing with the CML Debulking cocktail.

| Sample number | Frequence of CFC in CML bone marrow | Frequency of CFC following CML Debulking | Fold Enrichment | Recovery of CFC |
|---|---|---|---|---|
| 1 | 1:62 | 1:2.8 | 23 | 53 |
| 2 | 1:204 | 1:6.2 | 33 | 61 |
| 3 | 1:47 | 1:5.7 | 8.6 | 9.1 |
| Mean | 1:104 | 1:4.7 | 21 | 57 |

TABLE 2C

The Frequency and Recovery of Week 6 CFC in CML blood and bone marrow samples before and after processing with the CML debulking cocktail.

|   | Week 6 CFC: Nucleated Cells in Start | Week 6 CFC: Nucleated Cells Following CML De-Bulking | Fold Enrichment of Week 6 CFC | % Recovery of Week 6 CFC |
|---|---|---|---|---|
| 1 | 1:56980 | 1:11 | 1398 | 100 |
| 2 | 1:948 | 1:41 | 87 | 94 |

(Sample 1, Peripheral Blood: Sample 2, Bone Marrow)

TABLE 3A

Comparison of the purity, enrichment and yield of CD34+ cells obtained from CML low density blood or marrow samples using two different antibody cocktails to remove mature cells.

| | Purity (%) | | Enrichment (Fold) | | Recovery (%) | |
|---|---|---|---|---|---|---|
| CML Sample No. | Standard Cocktail | CML Debulking Cocktail | Standard Cocktail | CML Debulking Cocktail | Standard Cocktail | CML Debulking Cocktail |
| 1 | 32 | 36 | 23 | 26 | 67 | 47 |
| 2 | 36 | 55 | 22 | 33 | 19 | 35 |
| 3 | 39 | 54 | 27 | 37 | 16 | 11 |
| 4 | 64 | 80 | 14 | 17 | 45 | 40 |
| Mean ± SEM | 43 ± 7 | 56 ± 9* | 22 ± 3 | 28 ± 4* | 37 ± 12 | 33 ± 8** |

*0.05 > p > 0.01 (paired t-test) compared to values for the standard Ab cocktail.
**p > 0.05 (paired t-test) compared to values for the standard Ab cocktail.

TABLE 3B

Comparison of the frequency of CFC obtained from CML low density blood or bone marrow samples using two different antibody cocktails to remove mature cells.

| Sample Number | Standard Cocktail | CML Debulking Cocktail |
|---|---|---|
| 1 | 1:3.4 | 1:2.8 |
| 2 | 1:6.2 | 1:6.2 |
| 3 | 1:5.7 | 1:5.7 |
| 4 | 1:19.4 | 1:14.2 |
| Mean | 1:8.7 | 1:7.2 |

TABLE 4

Percent recovery of CD34+ cells and CFC after thawing ficolled low density cells or cells processed with the CML debulking cocktail

| | CD34+ | | CFC | |
|---|---|---|---|---|
| Sample No. | Low Density Cells | CML Debulking Cocktail | Low Density Cells | CML Debulking Cocktail |
| 1 | 0.8 | 12 | 6 | 18 |
| 2 | 2.5 | 29 | 32 | 72 |
| 3 | 1.2 | 44 | 1.7 | 60 |
| 4 | 0.3 | 102 | 1.4 | 123 |
| 5 | 3.7 | 118 | 0.4 | 15 |
| Mean ± SEM | 1.7 ± 0.6 | 61 ± 21* | 8.3 ± 6.0 | 58 ± 20* |

Recovery values are expressed as a percent of the total number of cells of the type assessed present in the correpsonding low density or lin- population prior to cryopreservation.
*0.05 > p > 0.01 (paired t-test) compared to values for low density cells.

We claim:

1. A method for depleting differentiated or lineage committed cells from a sample from a patient with chronic myeloid leukemia comprising:
   (a) reacting the sample with an antibody composition comprising antibodies specific for glycophorin A, CD2, CD3, CD14, CD15, CD16, CD19, CD24, CD56, CD66b and IgE under conditions so that conjugates form between the antibodies and cells in the sample having the antigens glycophorin A, CD2, CD3, CD14, CD15, CD16, CD19, CD24, CD56, CD66b and IgE on their surfaces;
   (b) removing the conjugates; and
   (c) recovering a cell preparation which is depleted of lineage committed cells.

2. A method for depleting differentiated or lineage committed cells from a sample from a patient with chronic myeloid leukemia according to claim 1 comprising:
   (a) reacting the sample with an antibody specific for CD15 under conditions so that conjugates form between the antibodies and cells in the sample having the antigen CD15 on their surfaces;
   (b) reacting the sample from step (a) with an antibody composition comprising antibodies specific for glycophorin A, CD2, CD3, CD14, CD16, CD19, CD24, CD56, CD66b and IgE under conditions so that conjugates form between the antibodies and the cells in the sample having the antigens glycophorin A, CD2, CD3, CD14, CD16, CD19, CD24, CD56, CD66b and IgE on their surfaces;
   (c) removing the conjugates; and
   (d) recovering a cell preparation which is depleted of lineage committed cells.

3. A method as claimed in claim 1 wherein the antibodies are monoclonal.

4. A method as claimed in claim 2 wherein the antibodies are monoclonal.

5. A method as claimed in claim 1 wherein the antibodies are labelled with a marker or they are conjugated to a matrix.

6. A method as claimed in claim 5 wherein the antibodies are labelled with biotin or a fluorochrome.

7. A method as claimed in claim 2, wherein each of the antibodies added in step (b) is incorporated in a tetrameric antibody complex wherein each tetrameric antibody complex comprises a first monoclonal antibody of a first animal species from the antibody composition added in step (b), and a second monoclonal antibody of the first animal species which is capable of binding to at least one antigen on the surface of a matrix, which have been conjugated to form a cyclic tetramer with two monoclonal antibodies of a second animal species directed against the Fc-fragments of the antibodies of the first animal species.

8. A method according to claim 7 further comprising adding an anti-biotin tetrameric antibody complex and the antibody specific for CD15 is biotinylated.

9. A method according to claim 2 wherein the sample is blood or bone marrow.

10. An antibody composition comprising antibodies specific for glycophorin A, CD2, CD3, CD14, CD15, CD16, CD19, CD24, CD56, CD66b and IgE.

11. An antibody composition comprising antibodies specific for glycophorin A, CD2, CD3, CD14, CD16, CD19, CD24, CD56, CD66b and IgE.

12. An antibody composition as claimed in claim 10 wherein the antibodies are monoclonal antibodies.

13. An antibody composition as claimed in claim 11 wherein the antibodies are monoclonal antibodies.

* * * * *